(12) United States Patent
Arai

(10) Patent No.: US 7,976,934 B2
(45) Date of Patent: Jul. 12, 2011

(54) CLOTH AND SOLID PIECE ASSEMBLY AND PRODUCTION METHOD FOR CLOTH AND SOLID PIECE ASSEMBLY

(75) Inventor: Yoshinobu Arai, Osaka (JP)

(73) Assignee: PIP Co., Ltd. (JP)

( * ) Notice: Subject to any disclaimer, the term of this patent is extended or adjusted under 35 U.S.C. 154(b) by 630 days.

(21) Appl. No.: 11/944,747

(22) Filed: Nov. 26, 2007

(65) Prior Publication Data

US 2008/0124519 A1 May 29, 2008

(30) Foreign Application Priority Data

Nov. 27, 2006 (JP) .................. 2006-319215

(51) Int. Cl.
*B32B 1/00* (2006.01)
*A61N 1/00* (2006.01)
*A61B 17/52* (2006.01)

(52) U.S. Cl. ....... 428/174; 428/178; 428/40.1; 428/900; 600/9; 600/15; 264/284; 264/293

(58) Field of Classification Search .................. 428/174, 428/178, 900, 40.1; 600/9, 15; 264/284, 264/293; 156/209, 219
See application file for complete search history.

(56) References Cited

U.S. PATENT DOCUMENTS

| | | | |
|---|---|---|---|
| 5,195,197 A | 3/1993 | Gutierrez et al. | |
| 2006/0287567 A1 | 12/2006 | Hsieh | |

FOREIGN PATENT DOCUMENTS

| | | |
|---|---|---|
| EP | 1 419 754 A1 | 5/2004 |
| JP | 2-215478 | 8/1990 |
| JP | 3011940 | 6/1995 |
| JP | 9-279458 | 10/1997 |
| JP | 2002000743 A * | 1/2002 |
| JP | 2005328907 A * | 12/2005 |

* cited by examiner

*Primary Examiner* — David R Sample
*Assistant Examiner* — Catherine Simone
(74) *Attorney, Agent, or Firm* — Gerald E. Hespos; Michael J. Porco

(57) ABSTRACT

Disclosed is a cloth and solid piece assembly, which comprises a cloth which is subjected to an embossing process to have a receiving portion formed through the embossing process in such a manner as to protrude from a surface of the cloth in a direction perpendicular to the surface to have an opening oriented in a direction opposite to the protruding direction, a solid piece received inside the receiving portion, and an adhesive material. The adhesive material is received inside the receiving portion and bonded to an inner peripheral surface of the receiving portion while plugging the opening of the receiving portion, so as to fix the solid piece inside the receiving portion. The cloth and solid piece assembly can reliably suppress peeling of a bonded region between the adhesive material and the cloth, in a simple structure.

16 Claims, 10 Drawing Sheets

CLOTH AND SOLID PIECE ASSEMBLY AND PRODUCTION METHOD FOR CLOTH AND SOLID PIECE ASSEMBLY

BACKGROUND OF THE INVENTION

1. Field of the Invention

The present invention relates to a cloth and solid piece assembly embedded with solid pieces, and a production method for the same.

2. Description of the Related Art

Heretofore, it has been noted that a magnetic flux or a negative ion applied to a human body can facilitate blood flow and provide favorable health effects, and therefore various types of health appliances have been developed to obtain such advantages.

For example, there has been known a garment comprising a cloth which fixedly holds a magnet generating a magnetic flux, wherein the garment is designed to apply a magnetic flux of the magnet to a body of a user when it is worn by the user. As such an assembly comprising a cloth and a solid piece, such as a magnet, fixed to the cloth, Japanese Registered Utility Model No. 3011940 (hereinafter, referred to as "Patent Publication") discloses a cloth and solid piece assembly comprising a woven or nonwoven cloth, a magnet mounted on the cloth in such a manner that at least a part of the magnet is sunk into the cloth, and an adhesive material fixing the magnet to the cloth. In this cloth and solid piece assembly, the magnet is fixed to the cloth by applying the adhesive material to cover over the magnet placed on the cloth and then melt-bonding the adhesive material to a portion of the cloth around a periphery of the magnet. That is, the adhesive material protrudes outwardly from a surface of the cloth.

The Patent Publication also discloses another embodiment where the adhesive material is meltingly bonded to the entire surface of the cloth while sandwiching the magnet therebetween. More specifically, a powder of ore having natural radioactivity, such as serpentine, and a powder of bryophyte, such as Polytrichum, are mixed in the adhesive material, and the cloth and solid piece assembly is used in such a manner as to allow the adhesive material to come into contact with a body of a user. This cloth and solid piece assembly has advantages of being able to allow medicinal benefits of the bryophyte to effectively act on the user's body, and facilitate blood flow by a magnetic flux from the magnet and a far-infrared ray from the ore.

In the above cloth and solid piece assembly, the adhesive material covers the magnet while protruding outwardly from the surface of the cloth. Thus, when the cloth and solid piece assembly is used as a garment, the adhesive material is likely to be rubbed against a body of a user and others during wearing of the garment and thereby peeled off from the cloth. If a melt-bonded area between the adhesive material and the cloth is increased, or the adhesive material is melt-bonded to the entire surface of the cloth as described above, so as to suppress the peeling of the adhesive material, an overall size of the cloth and solid piece assembly will become larger to cause a problem about unfavorable increase in cost.

SUMMARY OF THE INVENTION

In view of the above circumstances, it is an object of the present invention to provide a cloth and solid piece assembly capable of reliably suppressing peeling of a bonded region between an adhesive material and a cloth, in a simple structure or manner.

In order to achieve this object, according to an aspect of the present invention, a cloth and solid piece assembly comprises a cloth, and a solid piece fixed to the cloth. In this cloth and solid piece assembly, the cloth is subjected to an embossing process, and has a receiving portion formed through the embossing process in such a manner as to protrude from a first initial surface of the cloth in a direction perpendicular to the first initial surface to have an opening oriented in a direction opposite to the protruding direction and opened in a second initial surface of the cloth on an opposite side of the first initial surface. The solid piece is received inside the receiving portion, and an adhesive material is received inside the receiving portion and bonded to an inner peripheral surface of the receiving portion while plugging the opening of the receiving portion, so as to fix the solid piece inside the receiving portion.

As mentioned above, the present invention can provide a cloth and solid piece assembly capable of reliably suppressing peeling of a bonded region between the adhesive material and the cloth, in a simple structure or manner.

BRIEF DESCRIPTION OF THE PREFERRED EMBODIMENTS

With reference to drawings, a preferred embodiment of the present invention will now be described. The following description will be made based on one example where a cloth and solid piece assembly according to one embodiment of the present invention is used as a part of an undergarment, and a magnet is used as a solid piece to be fixedly embedded in the cloth and solid piece assembly.

Figure 1:
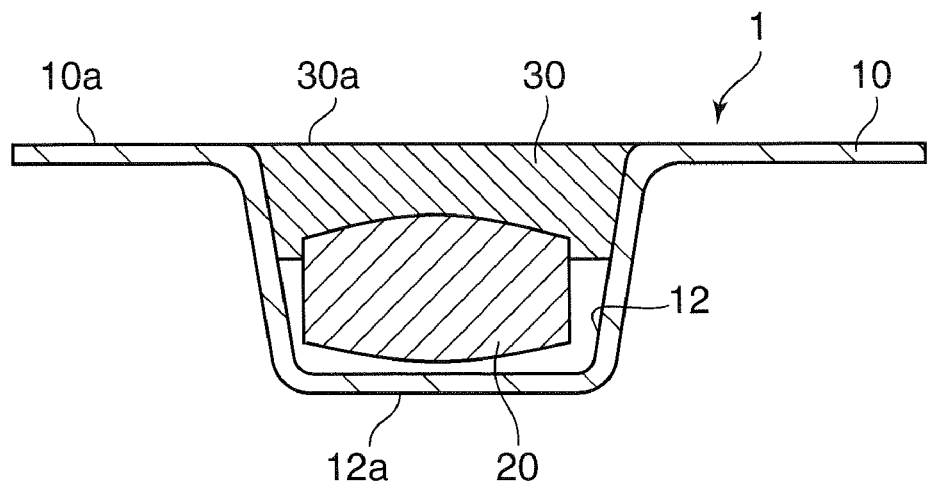
FIG. 1 is a fragmentary sectional view of a cloth and solid piece assembly according to one embodiment of the present invention.
Figure 2:
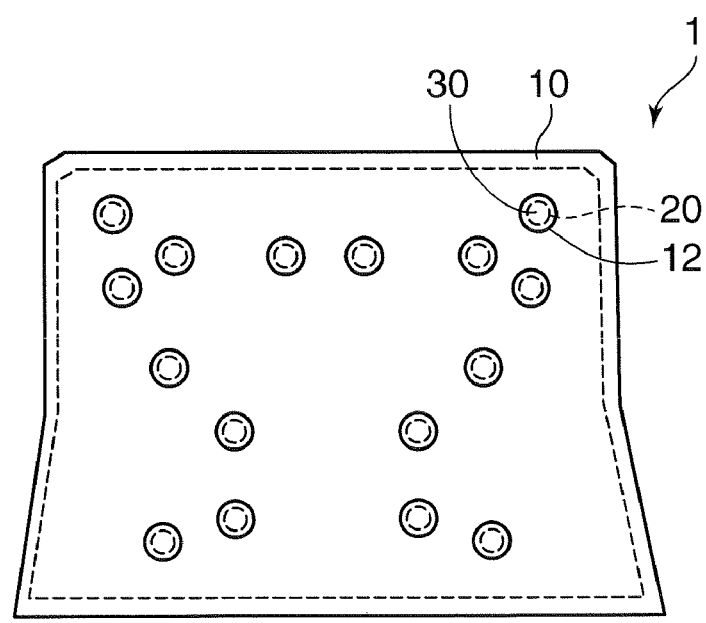
FIG. 2 is a front view of the cloth and solid piece assembly illustrated in FIG. 1.
Figure 3:
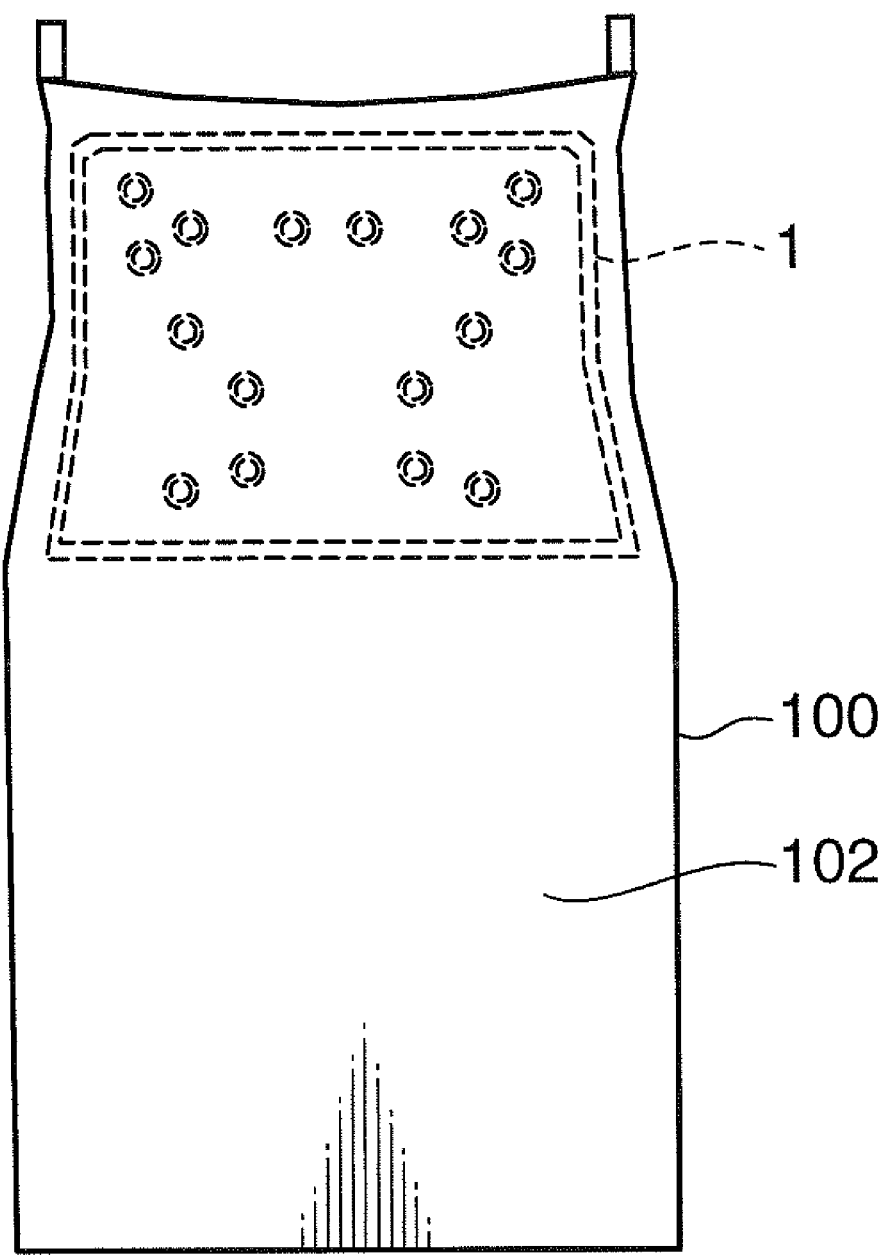
FIG. 3 is a front view of an undergarment mounted with solid-pieces, i.e. solid piece assembly illustrated in FIG. 1.

FIG. 1 is a fragmentary sectional view of a cloth and solid piece assembly according to one embodiment of the present invention, and FIG. 2 is a front view of the cloth and solid piece assembly. FIG. 3 is a front view of an undergarment mounting thereto the cloth and solid piece assembly, and FIG. 4 is a sectional view of the undergarment mounting.

Figure 4:
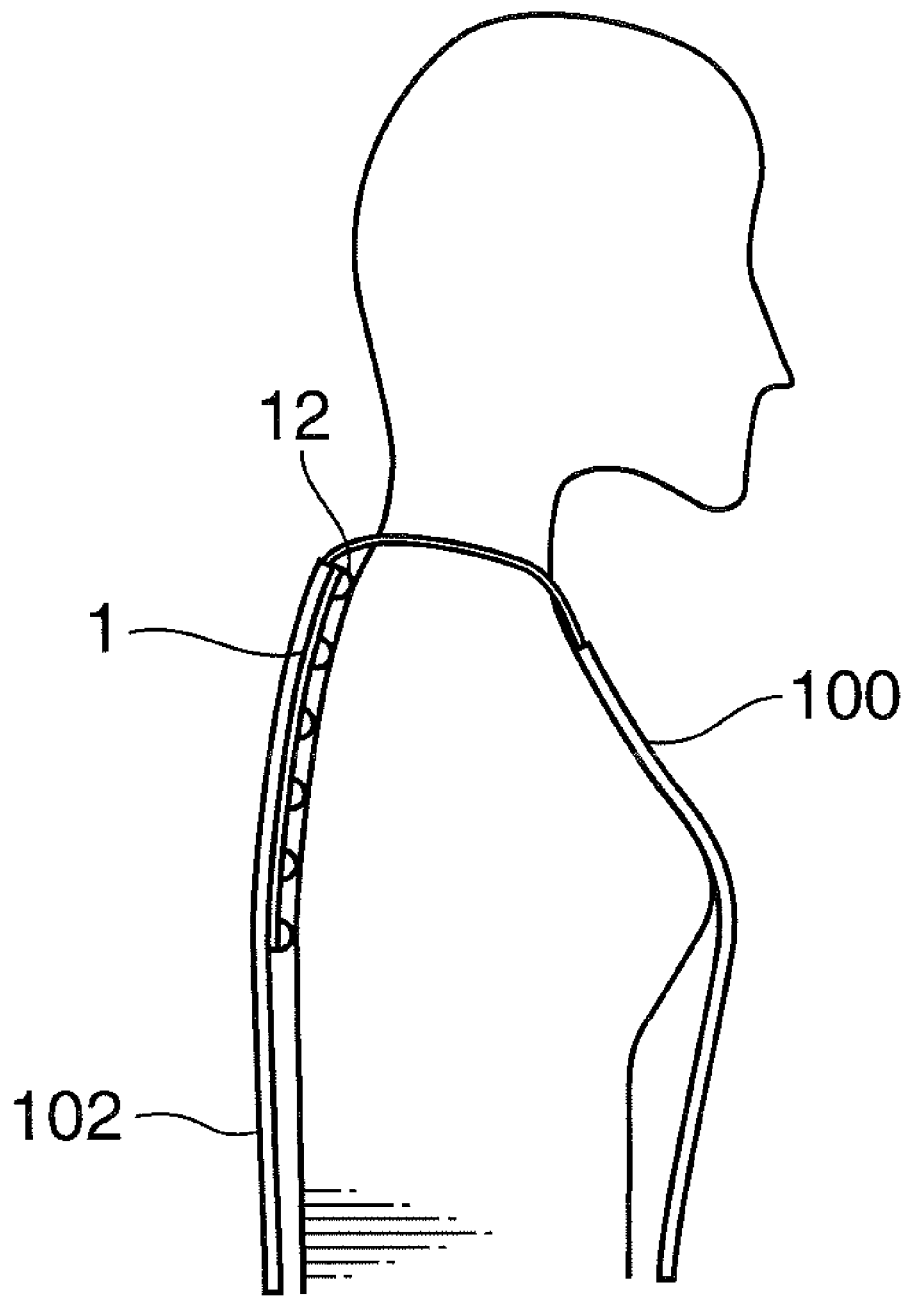
FIG. 4 is a schematic view of the undergarment illustrated in FIG. 3.

As shown in FIGS. 3 and 4, the cloth and solid piece assembly 1 is attached to a back portion of the undergarment 100. More specifically, the cloth and solid piece assembly 1 attached onto an inner surface of a rear body 102 adapted to cover over an entire back of a user, in the undergarment 100.

As shown in FIG. 1, the cloth and solid piece assembly 1 comprises a cloth 10, a plurality of magnets 20, and an adhesive material 30.

The cloth 10 consists of a woven cloth having the same composition as that of at least the rear body 102 of the undergarment 100, and has a size capable of covering respective central regions of a shoulder and a back of a user, as shown in FIG. 3. This cloth 10 has an outer peripheral portion sewn by a predetermined textile thread to prevent straggling of weaving yarns or the like. The cloth 10 has a plurality of receiving portions 12 each formed to protrude from a first initial surface (in FIG. 1, a lower surface) of the cloth 10 in a direction perpendicular to the first initial surface to have an opening oriented in a direction opposite to the protruding direction and opened in a second initial surface (in FIG. 1, an upper surface 10a) of the cloth 10 on a opposite side of the first initial surface.

As shown in FIG. 4, each of the receiving portions 12 is formed to protrude toward a body of a user in a state after the cloth 10 is attached onto the rear body 102 of the undergarment 100, and the undergarment 100 is worn by the user. Each of the receiving portions 12 is formed through an embossing process, so that a bottom wall 12a thereof extending in a direction perpendicular to the protruding direction has an approximately even thickness. Further, each of the receiving portions 12 is arranged at a position approximately corresponding to that of a trigger point in the user's back, when the undergarment 100 is worn by the user, i.e., during use.

Each of the plurality of magnets 20 is adapted to generate a magnetic flux so as to facilitate blood flow of the user's body by an action of the magnetic flux. For example, each of the magnets 20 consists of a ferrite magnet or a rare-earth magnet, and has a magnetic flux density of about 100 mT (milli-Tesla). Each of the magnets 20 is formed as a small piece having a shape (e.g., in a pellet or tablet shape) capable of being received inside a corresponding one of the receiving portions 12 formed in the cloth 10. Thus, during use, each of the magnets 20 received in the respective receiving portions 12 can apply a magnetic flux to the user's body through the bottom wall 12a in each of the receiving portions 12. Particularly, each of the receiving portions 12 is arranged at the position of the trigger point of the user's body as described above, and therefore a magnetic flux from each of the magnets received in the respective receiving portions 12 is effectively applied to the user's body during use. In addition, the bottom wall 12a in each of the receiving portions 12, i.e., a portion of the cloth 10 interposed between the user's body and each of the magnets 20 received in the respective receiving portions 12 during use, is formed to have an even thickness as described above, and therefore a magnetic flux from each of the magnets 20 is evenly applied to the user's body.

The adhesive material 30 serves as a means to fix each of the magnets 20 inside a corresponding one of the receiving portions 12. Specifically, in each of the receiving portions 12 receiving therein the respective magnets 20, the adhesive material 30 is bonded to an inner peripheral surface of the receiving portion 12 while plugging the opening of the receiving portion 12, so as to fix the magnet 20 inside the receiving portion 12.

The adhesive material 30 is received in the receiving portion 12 without a step between an outer surface 30a of the adhesive material 30 and the second initial surface 10a of the cloth 10. That is, the outer surface 30a of the adhesive material 30 is flush with the second initial surface 10a of the cloth 10 to provide a smooth top (in FIG. 1) surface to the cloth and solid piece assembly 1. Thus, when the cloth and solid piece assembly 1 is used in a garment, such as the undergarment 100, particularly, in such a manner that the protrusion of the receiving portion faces the user's body, the above configuration makes it possible to suppress a formation of irregularities in an outer surface of the cloth and solid piece assembly 1 and maintain the same shape as that of an undergarment devoid of the magnet 20, in outer appearance. Furthermore, the adhesive material 30 is received in the receiving portion 12, i.e., it is not attached to any portion other than the receiving portion 12. This makes it possible to suppress deterioration in air permeability or breathability of the cloth 10 due to the adhesive material 30.

For example, the adhesive material 30 may be made of a thermosetting silicone resin, as will be more specifically described later.

The cloth and solid piece assembly 1 having the magnets 20 fixed inside the respective receiving portions 12 through the adhesive material 30 in the above manner is attached to the inner surface of the rear body 102 of the undergarment 100. Thus, magnetic fluxes from the magnets 20 received in the respective receiving portions 12 will be applied to the user's body through the respective bottom walls 12a to facilitate blood flow of the user's body.

A production method of the cloth and solid piece assembly 1 will be described below.

1) Pre-Bonding Step 1-1) Sewing Step

Figure 5:
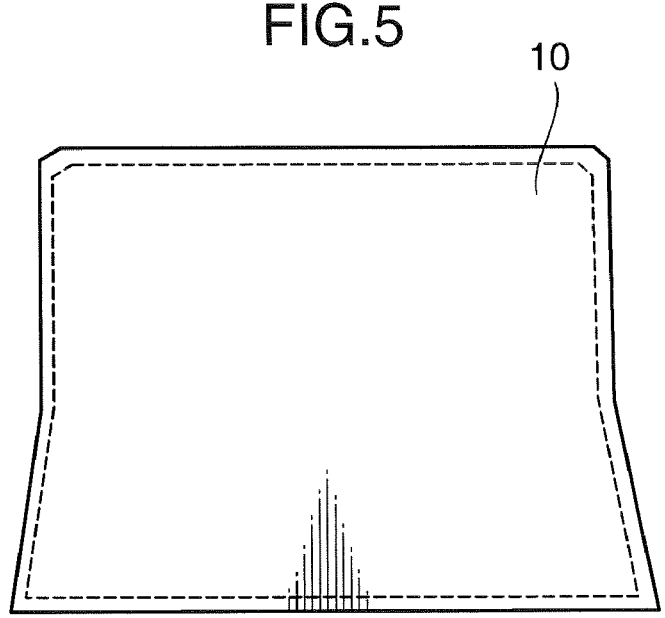
FIG. 5 is a front view of a cloth for the cloth and solid piece assembly illustrated in FIG. 1, in a state after being subjected to a sewing process.

A sewing step is intended to subject a cloth 10 before forming the receiving portions 12, to a sewing process. Specifically, in the sewing step, as shown in FIG. 5, an outer peripheral portion of the cloth 10 is sewn by a sewing machine or the like, to prevent straggling of weaving yarns which would otherwise occur from an outer peripheral edge of the cloth 10.

1-2) Needle Inspection Step

Figure 6:
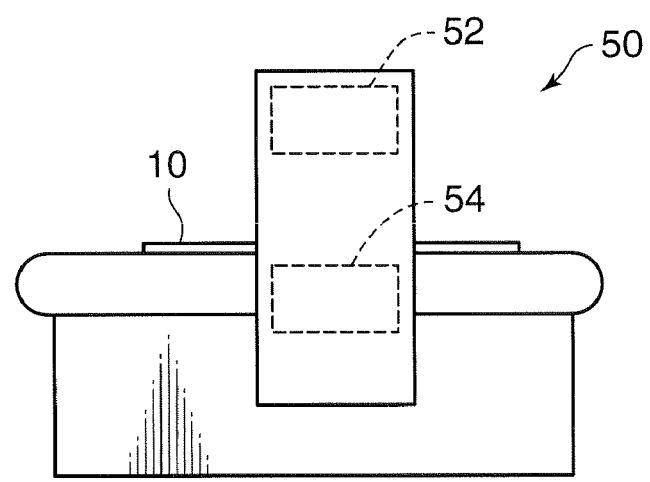
FIG. 6 is a schematic side view of the sewn cloth illustrated in FIG. 5, in a state when it is inspected by a needle detector.

A needle inspection step is intended to inspect whether a sewing needle, such as a broken portion of the sewing needle, is mixed, i.e., incorporated, in the cloth after the sewing step. Specifically, in the needle inspection step, as shown in FIG. 6, an inspection on whether a sewing needle is incorporated in the cloth 10 is performed using a needle detector 50. The needle detector 50 is provided with a permanent magnet 52 and a coil 54, and designed to detect an induced electromotive force to be generated in response to a change in magnetic field formed by the permanent magnet 52 and a coil 54. In this step, the inspection on whether a sewing needle is incorporated in the cloth 10 is performed depending on whether an induced electromotive force is detected, while moving the cloth 10 between the permanent magnet 52 and the coil 54. That is, if a sewing needle is incorporated in the cloth 10, an induced electromotive force will be generated when the sewing needle passes across the magnetic field. Thus, if an induced electromotive force is detected when the cloth 10 is moved between the permanent magnet 52 and the coil 54 to pass across the magnetic field, it can be determined that a sewing needle is incorporated in the cloth 10. The needle detector 50 is designed to blink a light or the like in response to generation of the induced electromotive force so as to inform an operator about abnormality. Then, when it is detected that a broken portion of the sewing needle is incorporated in the cloth 10, the needle is removed by the operator, and then the cloth 10 is re-inspected by the needle detector 50, for confirmation.

1-3) Material Placing Step

In a material placing step, an underlay-member placing step and a cloth placing step are performed.

1-3-1) Underlay-Member Placing step

Figure 7:
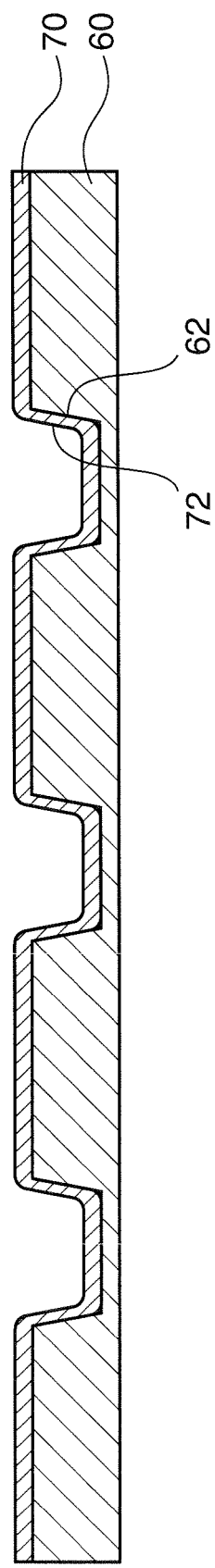
FIG. 7 is a sectional view showing a state after an underlay member is placed on a base.

The underlay-member placing step is intended to place an underlay member 70 on a base 60, as shown in FIG. 7. The base 60 is a female die adapted to form the receiving portions 12 in the cloth 10. The base 60 has a plurality of concave portions 62 each formed in a surface thereof to have approximately the same shape as that of the receiving portion 12. The underlay member 70 serves as a means to retain the shape of the receiving portion 12. In this embodiment, the underlay member 70 is formed of denim. The denim member 70 has a plurality of shape-retaining portions 72 formed in a surface thereof at positions corresponding to the respective concave portions 62 in such a manner as to protrude toward the respective concave portions 62 and each have a shape capable of receiving therein a corresponding one of the receiving portions 12. In the underlay-member placing step, the denim member 70 is placed on the base 60 in such a manner that the shape-retaining portions 72 are fitted into the respective concave portions 62.

1-3-2) Cloth Placing Step

Figure 8:
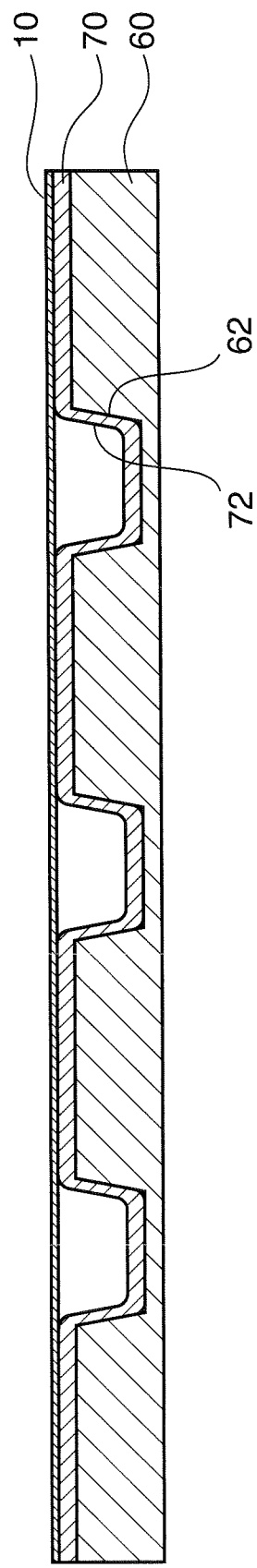
FIG. 8 is a sectional view showing a state after a cloth is placed on the underlay member illustrated in FIG. 7.

In the cloth placing step, as shown in FIG. 8, the cloth 10 after the needle inspection step is placed on the denim member 70 placed on the base 60.

1-4) Embossing Step

Figure 9:
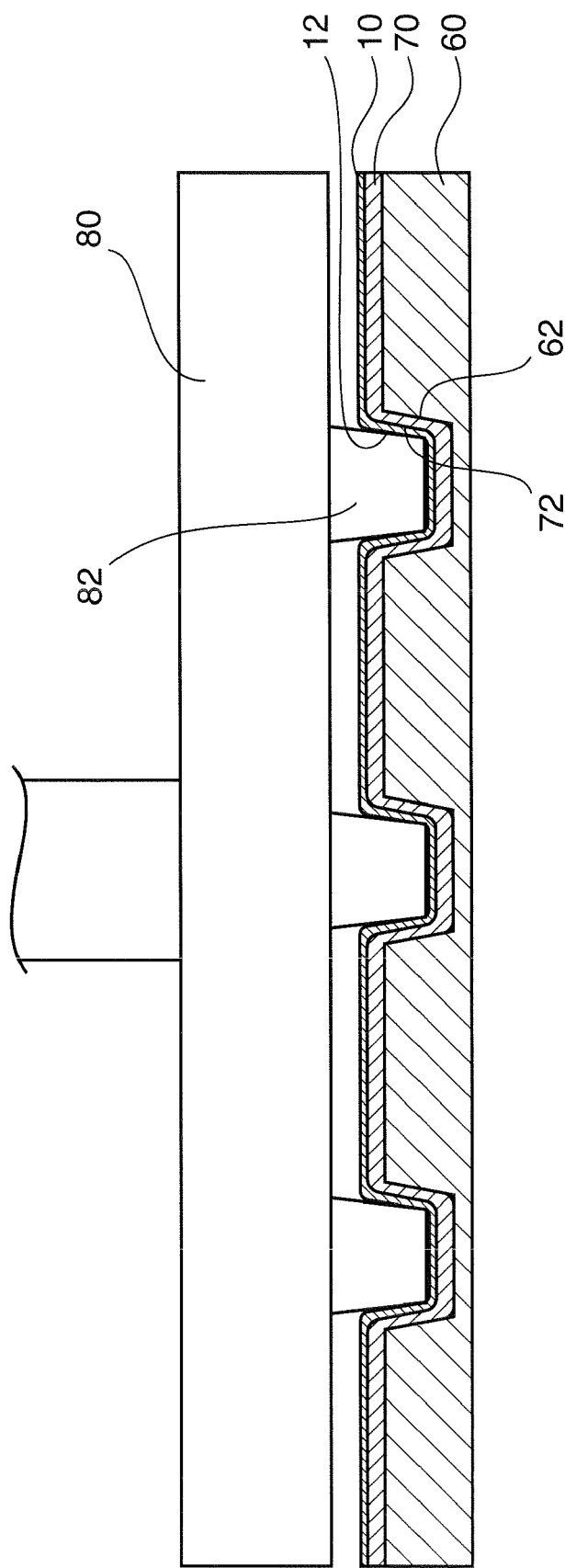
FIG. 9 is a sectional view showing a state after a receiving portion is formed in the cloth in FIG. 8.

An embossing step is intended to subject the cloth 10 to an embossing process so as to form the receiving portions 12 in the cloth 10, as shown in FIG. 9. Specifically, in the embossing step, the cloth 10 is pressed by a pressing member 80, to form the receiving portions 12. The pressing member 80 is a male die adapted to form the receiving portions 12 in the cloth 10. The pressing member 80 has a plurality of convex portions 82 formed in a surface thereof in such a manner as to protrude toward the base 60. Each of the convex portions 82 has a shape fittable into a corresponding one of the concave portions 62 of the base 60 and a corresponding one of the shape-retaining portions 72 of the denim member 70. In the embossing step, the cloth 10 is pressed toward the base 60 by the convex portions 82, to form the receiving portions 12 between corresponding ones of the convex portions 82 and the shape-retaining portions 72 located on the respective concave portions 62.

Each of the convex portions 82 is designed to press the cloth 10 with an even pressing force, so that the bottom wall 12a in each of the receiving portion 12 can have an approximately even thickness.

2) Solid Piece Setting Step

Figure 10:
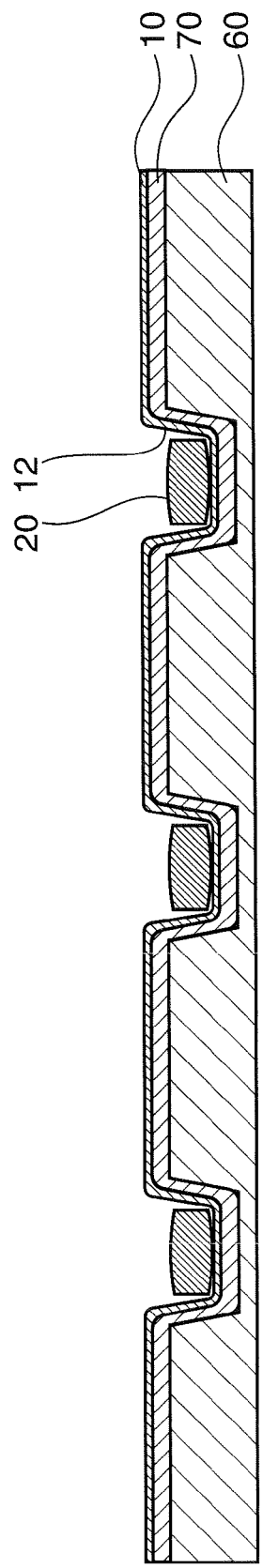
FIG. 10 is a sectional view showing a state after a magnet is set in the receiving portion in FIG. 9.

In a solid piece setting step, as shown in FIG. 10, the plurality of magnets are set in the respective receiving portions 12 formed through the embossing step.

3) Bonding Step

A bonding step is intended to drip the adhesive material 30 into each of the receiving portions 30 and bond the adhesive material 30 to the inner peripheral surface of the receiving portion 12.

Figure 11:
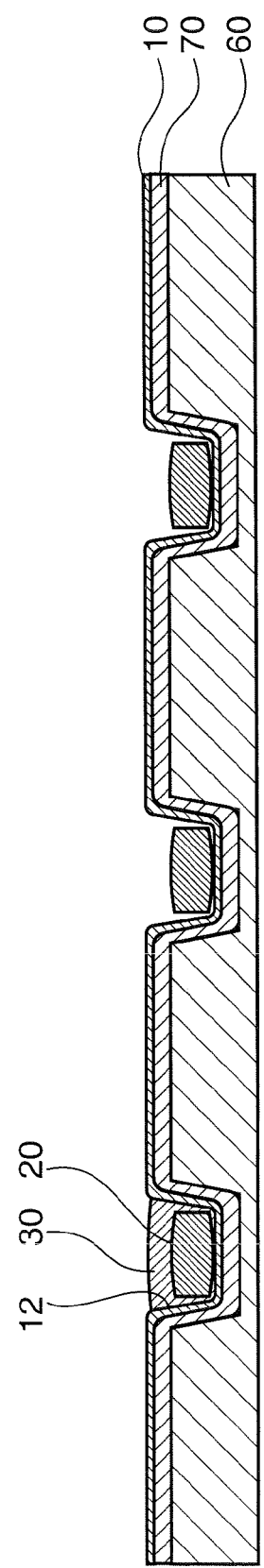
FIG. 11 is a sectional view showing a state after an adhesive material is dripped into the receiving portion illustrated in FIG. 10.

In the bonding step, as shown in FIG. 11, the adhesive material 30 is dripped into the receiving portion 12 using a dispenser (not shown) or the like. Particularly, in the bonding step, the adhesive material 30 is dripped while preventing a step from being defined between the outer surface 30a of the adhesive material 30 and the second initial surface 10a of the cloth.

Preferably, the adhesive material 30 has a property that it is increased in viscosity (i.e., hardened) after being dripped into the receiving portion 12a to an extent allowing a shape thereof to be stably maintained. The hardening process may be natural hardening, or may be forced hardening based on ultraviolet light irradiation or heating. More preferably, the adhesive material 30 has a property that a certain level of resilience (flexibility) is ensured even after being hardened. These properties of the adhesive material 30 make it possible to suppress crack, chap or breakage in the adhesive material 30 which would otherwise occur when an external force is applied to the adhesive material 30 during use. For example, a thermosetting silicone resin is suitably used as the adhesive material 30.

Figure 12:
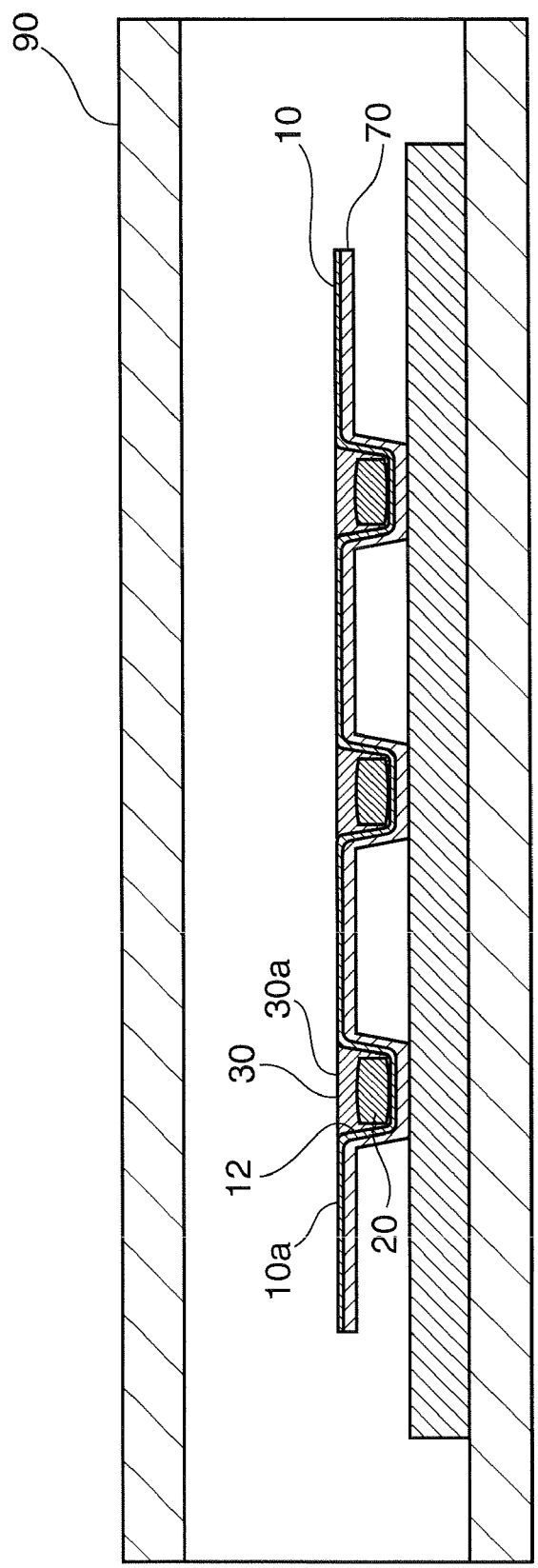
FIG. 12 is a sectional view showing a state when the cloth illustrated in FIG. 11 after dripping of the adhesive material is set in a drying machine.

As also shown in FIG. 12, the cloth 10 after dripping the adhesive material 30 is detached from the base 60 while being still placed on the denim member 70, and carried in a drying machine 90 together with the denim member 70. Then, the adhesive material 30 dripped into each of the receiving portions 12 is heatedly hardened in the drying machine 90, and bonded to the inner peripheral surface of the receiving portion 12. When the adhesive material 30 is hardened and bonded to the inner peripheral surface of the receiving portion 12, the magnet 20 received in the receiving portion 12 is fixed inside the receiving portion 12.

The cloth and solid piece assembly 1 produced in the above manner is attached to a rear body of an undergarment 100 in such a manner that the protrusions of the receiving portions 12 face a body of a user during use. Specifically, the cloth and solid piece assembly 1 is fixedly attached to the rear body of the undergarment 100 after completion of a sewing process, through an adhesive sheet or the like, for example, by an ultrasonic melt-bonding process.

As mentioned above, in the cloth and solid piece assembly 1 according to this embodiment, the magnet 20 is reliably fix to the cloth 10 while suppressing a protrusion of the adhesive material 30 relative to the second initial surface of the cloth 10, based on the simple structure where the opening of the receiving portion 12 receiving the magnet 20 therein is plugged by the adhesive material 30, and the adhesive material 30 is bonded to the inner peripheral surface of the receiving portion 20. Further, the cloth and solid piece assembly can suppress peeling of the adhesive material 30 due to rubbing against a body of a user and others.

In cases where the cloth and solid piece assembly 1 is used in an article, such as the undergarment 100, in such a manner as to be in contact with a body of a user during use, the magnet 20 received in the receiving portion 12 will more reliably come into contact with the user's body so as to efficiently exert the blood flow-facilitatory effect of the magnet 20 on the user's body. In addition, a direct contact between the adhesive material 30 and the user's body can be avoided to suppress a load on skin of the user so as to provide comfortable feeling to the user during use, even if the user has delicate skin. Further, the receiving portion 12 is formed through an embossing process, and therefore the bottom wall 12a of the receiving portion 12 interposed between the user's body and the magnet 20 during use has an even thickness. This makes it easy to manage the action of the magnet 20 to be exerted on the user's body through the bottom wall 12a.

In the cloth and solid piece assembly 1, the adhesive material 30 is formed without a step between the outer surface 30a of the adhesive material 30 and the second initial surface 10a of the cloth 10, as described above. This makes it possible to suppress a formation of irregularities in the outer surface of the cloth and solid piece assembly 1 so as to provide enhanced outer appearance.

In the aforementioned process as a method for producing the cloth and solid piece assembly 1, after placing the cloth 10 through the cloth placing step, the receiving portion 12 can be readily formed in the placed cloth 10 through the embossing step. Further, the magnet 20 is set in the receiving portion 20 through the solid piece setting step, and the adhesive material 30 is dripped into the receiving portion 12 while being bonded to the inner surface of the receiving portion 12, through the bonding step. Through these steps, the opening of the receiving portion 12 is plugged by the adhesive material 30, while receiving the magnet 20 inside the receiving portion. This makes it possible to fix the magnet 20 inside the receiving portion 12. Particularly, in the bonding step, the adhesive material 30 is dripped while preventing a step from being defined between the outer surface 30a of the adhesive material and the second initial surface 10a of the cloth 10. This makes it possible to readily provide a smooth outer surface to the cloth and solid piece assembly 1.

Further, the sewing step of subjecting the cloth 10 to a sewing process, and the needle inspection step of inspecting whether a sewing needle is incorporated in the sewn cloth 10, are performed before the solid piece setting step. Then, the magnet 20 is fixed to the cloth 10 through the adhesive material 30. This makes it possible to eliminate the need for performing an additional needle inspection step after the solid piece setting step, so as to efficiently produce the cloth and solid piece assembly 1.

In the material placing step, the denim member 70 having a thickness greater than that of the cloth 10 is placed on the base 60 (underlay-member placing step), and the cloth 10 is placed on the denim member 70 (cloth placing step). Then, each of the embossing step, the solid piece setting step and the bonding step is performed under the condition that the cloth 10 is placed on the denim member 70. Thus, a shape of the receiving portion 12 formed in the cloth 10 is adequately retained by the shape-retaining portion 72 formed in the denim member 70. This makes it possible to allow the magnet 20 and the adhesive material 30 to be stably received in the receiving portion 12, and prevent the shape of the receiving portion 12 from becoming misshapen during transportation between respective steps. This technique is effective, particularly, when the solid piece, such as the magnet 20, is fixed to the cloth 10 which has difficulty in retaining the shape of the receiving portion 12 due to a relatively small thickness thereof.

The above embodiment has been described based on one example where the cloth and solid piece assembly 1 is attached to the inner surface of the rear body 102 of the undergarment 100. Alternatively, an entirety of the rear body 102 may be formed of the cloth and solid piece assembly 1. Further, the cloth and solid piece assembly 1 may be used in a bed sheet, a cushion or the like, as well as a garment 100.

The above embodiment has been described based on one example where the magnet 20 is used as a solid piece to be fixed to the cloth 10. Alternatively, any other suitable solid piece having a potential to exert a blood flow-facilitatory effect, such as germanium and titanium, may be used.

The underlay member to be placed on the base 60 in the underlay-member placing step is not limited to the denim member 70, but may be any other suitable material capable of retaining the shape of the receiving portion 12 of the cloth 10, such as a relatively thick paper. However, a denim fabric is suitable as the underlay member, because it is relatively thick and excellent in shape-retaining performance. Preferably, the underlay member has heat shrinkability at the same level as that of the cloth 10, so as not to hinder heat shrinkage of the cloth 10 during heating using the drying machine 90 in the bonding step. Further, the cloth 10 may be placed directly on the base 10 by omitting the underlay-member placing step.

The sequence of the pre-bonding step is not limited to the aforementioned order. The point is that the sewing step and the needle inspection step are completed before the solid piece setting step of setting the magnet 20 in the receiving portion 12. Thus, the material placing step and/or the embossing step may be performed before the sewing step and the needle inspection step.

A material for use in the adhesive material 30 is not limited to the aforementioned specific one.

An arrangement of the solid piece, such as the magnet 20, is not limited to the aforementioned specific one.

Further, the needle detector 50 for use in the needle detection step is not limited to the type of detecting an induced electromotive force, but may be any other suitable type, such as a type using an X-ray.

As described above, an inventive cloth and solid piece assembly comprises a woven or nonwoven cloth, and a solid piece fixed to the cloth through an adhesive material. In this cloth and solid piece assembly, the cloth being subjected to an embossing process, and has a receiving portion formed through the embossing process in such a manner as to protrude from a first initial surface of the cloth in a direction perpendicular to the first initial surface to have an opening oriented in a direction opposite to the protruding direction and opened in a second initial surface of the cloth on a opposite side of the first initial surface. The solid piece is formed as a small piece and received inside the receiving portion, and the adhesive material is received inside the receiving portion and bonded to an inner peripheral surface of the receiving portion while plugging the opening of the receiving portion, so as to fix the solid piece inside the receiving portion.

In the cloth and solid piece assembly, the solid piece is reliably fixed to the cloth based on a simple structure where the solid piece is received in the receiving portion formed through an embossing process, and the opening of the receiving portion receiving the solid piece therein is plugged by the adhesive material. Further, in the cloth and solid piece assembly, the adhesive material fixing the solid piece is bonded to the inner peripheral surface of the receiving portion protruding from the first initial surface of the cloth, to suppress an outward protrusion of the adhesive material relative to the second initial surface of the cloth. Thus, the solid piece is reliably fixed to the cloth while suppressing a protrusion of the adhesive material relative to the cloth to prevent peeling of the adhesive material from the cloth due to rubbing against a body of a user and others.

Preferably, the cloth and solid piece assembly may be used in an article including a garment and a bed clothing, in such a manner as to be in contact with a body of a user during use, although the use of the cloth and solid piece assembly is not limited to this manner. In cases where the cloth and solid piece assembly is used in the above article, such as a garment and a bed clothing, it is preferable that the solid piece is made of a material which has a blood flow-facilitatory effect and includes a magnet, and the receiving portion is arranged to protrude toward the user's body during use.

The receiving portion arranged to protrude toward the user's body during use allows the solid piece, such as a magnet, to more reliably come into contact with the user's body so as to efficiently exert the blood flow-facilitatory effect of the solid piece on the user's body. In addition, a direct contact between the adhesive material and the user's body can be avoided to provide comfortable feeling to the user during use, even if the user has delicate skin. Further, the receiving portion is formed through an embossing process as described above, and therefore a portion of the cloth interposed between the user's body and the solid piece, such as a magnet, during use has an even thickness. This makes it easy to manage the action of the solid piece, such as a magnet, to be exerted on the user's body through the cloth. The material of the solid piece having a blood flow-facilitatory effect may include germanium and titanium, as well as a magnet.

Preferably, in the cloth and solid piece assembly, the adhesive material may be formed in a shape having an outer surface which prevents a step from being defined relative to the second initial surface of the cloth.

According to this feature, the cloth and solid piece assembly can ensure flatness and smoothness of the second initial surface without irregularity while fixing the solid piece. This provides enhanced appearance when the cloth and solid piece assembly is used in a garment or the like.

Preferably, in the cloth and solid piece assembly, at least a part of the cloth may be subjected to a sewing process.

According this feature, in the case of making the cloth and solid piece assembly into a garment or the like, straggling of weaving yarns in an edge of the cloth and solid piece assembly can be suppressed to facilitate tailoring so as to provide enhanced usability.

Also, an inventive method for producing the above cloth and solid piece assembly, comprises a material placing step of placing a cloth before forming the receiving portion, on a base having a concave portion in a surface thereof, an embossing step of pressing the cloth placed on the base, by a pressing member having a convex portion fittable into the concave portion, to form the receiving portion at a position where the cloth is partly pressed between the concave portion and the convex portion, a solid piece setting step of setting the solid piece in the receiving portion, and a bonding step of dripping the adhesive material into the receiving portion in such a manner as to plug the opening of the receiving portion while allowing the adhesive material to be bonded to an inner surface of the receiving portion.

In the method, in the material placing step, the cloth placed on the base having the concave portion may be pressed by the pressing member having the convex portion, through the embossing process. This makes it possible to readily form the receiving portion. Subsequently, in the setting step, the solid piece may be set in the receiving portion. Then, in the bonding step, the adhesive material may be dripped into the receiving portion in such a manner as to plug the opening of the receiving portion while allowing the adhesive material to be bonded to an inner surface of the receiving portion. This makes it possible to fix the solid piece inside the receiving portion in a relatively easy manner.

Furthermore, an inventive method for producing the cloth and solid piece assembly at least a part of which is subjected to a sewing process, comprises a pre-bonding step of subjecting a cloth before forming the receiving portion, to a sewing process, and forming the receiving portion in the sewn cloth, a solid piece setting step of setting the solid piece in the receiving portion, and a bonding step of dripping the adhesive material into the receiving portion in such a manner as to plug the opening of the receiving portion while allowing the adhesive material to be bonded to an inner surface of the receiving portion. The pre-bonding step includes a sewing step of sewing at least a part of the cloth using a sewing needle, a needle inspection step of inspecting whether the sewing needle is incorporated in the sewn cloth, a material placing step of placing the cloth after the needle inspection step, on a base having a concave portion in a surface thereof, and an embossing step of pressing the cloth placed on the base, by a pressing member having a convex portion fittable into the concave portion, to form the receiving portion at a position where the cloth is partly pressed between the concave portion and the convex portion.

In this method, in the pre-bonding step, the cloth may be subjected to a sewing process, and the receiving portion may be formed in the sewn cloth. Subsequently, in the setting step, the solid piece may be set in the receiving portion. Then, in the bonding step, the adhesive material may be dripped into the receiving portion in such a manner as to plug the opening of the receiving portion while allowing the adhesive material to be bonded to the inner surface of the receiving portion. This makes it possible to produce a cloth and solid piece assembly in which the solid is reliably fixed to the cloth and at least a part of which is subjected to a sewing process.

Further, the pre-bonding step may include the sewing step of sewing at least a part of the cloth using a sewing needle, and the needle inspection step of inspecting whether the sewing needle is incorporated in the sewn cloth. That is, the needle inspection step is performed before the solid piece is set in the receiving portion through the setting step. This makes it possible to avoid an undesirable situation where the solid piece is erroneously detected as a sewing needle during the needle inspection step, so as to efficiently perform the needle inspection step. For example, during a needle inspection step using a metal detector, under conditions that a metal sewing needle is used as the sewing needle, and a metal body, such as a magnet, serving as the solid piece, is set in the receiving portion, this method can prevent the solid piece from being picked up by the metal detector. That is, no sewing process is performed after the solid piece setting step, and therefore an erroneous incorporation of the sewing needle can be reliably detected only through the needle inspection step before the solid piece setting step, without the need for re-performing an additional needle inspection step after the solid piece setting step.

Preferably, in the above methods, the material placing step may include an underlay-member placing step of placing, on the base, an underlay member which has a shape-retaining portion formed at a position corresponding to the concave portion of the base in such a manner as to protrude toward the concave portion of the base and have a shape capable of receiving the receiving portion therein, and a cloth placing step of placing the cloth before forming the receiving portion, on the placed underlay member, wherein each of the embossing step, the solid piece setting step and the bonding step is performed under a condition that the cloth is placed on the underlay member.

According to this feature, in the material placing step, the cloth is placed on the underlay member placed through the underlay-member placing step. Then, each of the subsequent steps from the embossing step to the bonding step is performed under a condition that the cloth is placed on the underlay member. Thus, each of the subsequent steps can be performed under a condition that a shape of the receiving portion formed in the cloth is adequately retained by the shape-retaining portion formed in the underlay member. This makes it possible to more stably set the solid piece in the receiving portion, and more stably drip the adhesive material into the receiving portion.

This application is based on Japanese Patent application No. 2006-319215 filed in Japan Patent Office on Nov. 27, 2006, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A cloth and solid piece assembly comprising:
a cloth having a first surface to face a body of a user and a second surface opposite to said first surface, and a receiving portion protruding from said first surface in a direction perpendicular to said first surface to have an opening oriented in a direction opposite to said protruding direction and opened in said second surface;
a solid piece placed inside said receiving portion;
an adhesive material placed inside said receiving portion and bonded to an inner peripheral surface of said receiving portion while plugging said opening of said receiving portion, so as to fix said solid piece inside said receiving portion, and an outer surface of said adhesive material being flush with the second surface.

2. The cloth and solid piece assembly as defined in claim 1, which is used in an article including a garment and a bed clothing, in such a manner as to be in contact with a body of a user during use, wherein:
said receiving portion is arranged to protrude toward said user's body during use.

3. The cloth and solid piece assembly as defined in claim 1, wherein said adhesive material is formed in a shape having an outer surface which prevents a step from being defined relative to said second surface of said cloth.

4. The cloth and solid piece assembly as defined in claim 1, wherein at least a part of said cloth is sewed.

5. A method for producing the cloth and solid piece assembly as defined in claim 1, comprising:
a material placing step of placing a cloth before forming said receiving portion on a base having a concave portion in a surface thereof;
an embossing step of pressing said cloth placed on said base, by a pressing member having a convex portion fittable into said concave portion, to form said receiving portion at a position where said cloth is partly pressed between said concave portion and said convex portion;
a solid piece setting step of setting said solid piece in said receiving portion; and
a bonding step of dripping said adhesive material into said receiving portion in such a manner as to plug said opening of said receiving portion while allowing said adhesive material to be bonded to an inner surface of said receiving portion.

6. The method of claim 5, wherein said material placing step includes:
an underlay-member placing step of placing, on said base, an underlay member which has a shape-retaining portion formed at a position corresponding to said concave portion of said base in such a manner as to protrude toward said concave portion of said base and have a shape capable of receiving said receiving portion therein; and
a cloth placing step of placing the cloth before forming said receiving portion, on said placed underlay member wherein each of said embossing step, said solid piece setting step and said bonding step is performed under a condition that said cloth is placed on said underlay member.

7. A method for producing the cloth and solid piece assembly as defined in claim 4, comprising:
a pre-bonding step of subjecting a cloth before forming said receiving portion, to a sewing process, and forming said receiving portion in said sewn cloth;
a solid piece setting step of setting said solid piece in said receiving portion; and
a bonding step of dripping said adhesive material into said receiving portion in such a manner as to plug said opening of said receiving portion while allowing said adhesive material to be bonded to an inner surface of said receiving portion,
wherein said pre-bonding step includes:
a sewing step of sewing at least a part of said cloth using a sewing needle;
a needle inspection step of inspecting whether said sewing needle is incorporated in said sewn cloth;
a material placing step of placing said cloth after said needle inspection step, on a base having a concave portion in a surface thereof; and
an embossing step of pressing said cloth placed on said base, by a pressing member having a convex portion fittable into said concave portion, to form said receiving portion at a position where said cloth is partly pressed between said concave portion and said convex portion.

8. The method as defined in claim 7, wherein said material placing step includes:
an underlay-member placing step of placing, on said base, an underlay member which has a shape-retaining portion formed at a position corresponding to said concave portion of said base in such a manner as to protrude toward said concave portion of said base and have a shape capable of receiving said receiving portion therein; and
a cloth placing step of placing the cloth before forming said receiving portion, on said placed underlay member,
wherein each of said embossing step, said solid piece setting step and said bonding step is performed under a condition that said cloth is placed on said underlay member.

9. The cloth and solid piece assembly as defined in claim 1, wherein said solid piece includes germanium.

10. The cloth and solid piece assembly as defined in claim 1, wherein said solid piece includes titanium.

11. The cloth and solid piece assembly as defined in claim 1, wherein said solid piece includes germanium and titanium.

12. The cloth and solid piece assembly as defined in claim 1, wherein said adhesive material is made of a thermosetting silicone resin.

13. An item of clothing, comprising:
an outer fabric having an inner surface for facing toward a wearer and an outer surface opposite the inner surface;
a cloth having a first surface for facing the wearer and a second surface opposite to said first surface, and a plurality of spaced apart receiving portions protruding convexly from the first surface and defining a plurality of spaced apart concave regions open in the second surface;
solid pieces placed respectively in said concave regions of said receiving portions; and
an adhesive material placed in the concave regions of said receiving portions and bonded to inner peripheral surfaces of said concave regions of said receiving portions while plugging said openings of said receiving portions so as to fix said solid pieces inside the concave regions of said receiving portion, outer surface areas defined by said adhesive material being flush with areas of the second surface of said cloth adjacent the respective concave region, said areas of the second surface of said cloth adjacent the concave regions and the outer surface areas of the adhesive material being in substantially face-to-face contact with the inner surface of the outer fabric.

14. The item of clothing of claim 13, wherein the outer fabric and the cloth have the same composition.

15. The item of clothing of claim 13, wherein said solid piece includes a magnet.

16. The item of clothing of claim 13, wherein said adhesive material is made of a thermosetting silicone resin.

* * * * *